United States Patent
Shen

(10) Patent No.: US 10,918,501 B2
(45) Date of Patent: Feb. 16, 2021

(54) POLYCENTRIC KNEE JOINT HAVING AN ADJUSTMENT-FREE MULTI-STAGE AIR CYLINDER

(71) Applicant: Pro Limb International Corp., New Taipei (TW)

(72) Inventor: Hsin-Fa Shen, New Taipei (TW)

(73) Assignee: PRO LIMB INTERNATIONAL CORP., New Taipei (TW)

( * ) Notice: Subject to any disclaimer, the term of this patent is extended or adjusted under 35 U.S.C. 154(b) by 0 days.

(21) Appl. No.: 16/428,435

(22) Filed: May 31, 2019

(65) Prior Publication Data

US 2019/0282379 A1    Sep. 19, 2019

Related U.S. Application Data

(63) Continuation-in-part of application No. 15/809,222, filed on Nov. 10, 2017, now abandoned, which is a
(Continued)

(30) Foreign Application Priority Data

Apr. 5, 2012 (TW) .............................. 101206148 A

(51) Int. Cl.
*A61F 2/68* (2006.01)
*A61F 2/64* (2006.01)
*A61F 2/74* (2006.01)

(52) U.S. Cl.
CPC ................ *A61F 2/68* (2013.01); *A61F 2/644* (2013.01); *A61F 2002/747* (2013.01); *A61F 2002/748* (2013.01)

(58) Field of Classification Search
CPC ...... F15B 15/149; F15B 15/204; A61F 2/602; A61F 2/644; A61F 2002/5003; A61F 2002/747
See application file for complete search history.

(56) References Cited

U.S. PATENT DOCUMENTS 2,208,275 A * 7/1940 Conner ................... A61F 2/644
                                                          623/46
2,842,159 A    7/1958 Sprague
(Continued)

FOREIGN PATENT DOCUMENTS

DE          332451 C     1/1921
GB          724062 A     2/1955
(Continued)

OTHER PUBLICATIONS

"Balance Knee OFM1/KFM1 Instructions for Use," OSSUR, 2017, 89 Pages.
(Continued)

*Primary Examiner* — Abiy Teka
*Assistant Examiner* — Matthew Wilblin
(74) *Attorney, Agent, or Firm* — Workman Nydegger

(57) ABSTRACT

A polycentric knee joint including an adjustment-free multi-stage prosthesis air cylinder. The air cylinder has an air cylinder body, a piston assembly slidably mounted on the air cylinder body, a first check valve mounted in the piston, and a multi-stage air pressure valve mounted inside a lower air way of the air cylinder body. The multi-stage air pressure valve automatically cushions movements of the piston assembly without being adjusted whenever a user of the prosthesis joint walks slowly or quickly, for improved comfort.

17 Claims, 12 Drawing Sheets

Related U.S. Application Data continuation-in-part of application No. 13/846,026, filed on Mar. 18, 2013, now abandoned.

(56) References Cited

U.S. PATENT DOCUMENTS

| | | | |
|---|---|---|---|
| 3,593,616 A | | 7/1971 | Fox |
| 3,875,850 A | | 4/1975 | Reynolds et al. |
| 4,386,766 A | | 6/1983 | Bauer et al. |
| 4,727,903 A | | 3/1988 | Sturgis et al. |
| 5,085,246 A | | 2/1992 | Griinke |
| 5,273,141 A | | 12/1993 | Veret et al. |
| 5,400,694 A | | 3/1995 | Bartlett |
| 5,522,422 A | | 6/1996 | Beck |
| 5,746,774 A | * | 5/1998 | Kramer .................. A61F 2/644 623/39 |
| 6,086,616 A | * | 7/2000 | Okuda .................. A61F 2/644 623/44 |
| 6,558,430 B1 | * | 5/2003 | Nakaya .................. A61F 2/64 188/313 |
| 6,920,895 B2 | | 7/2005 | Avis et al. |
| 7,784,392 B1 | | 8/2010 | Manney, III |
| 9,775,715 B2 | * | 10/2017 | Boiten .................. A61F 2/644 |
| 2002/0026246 A1 | * | 2/2002 | Suzuki .................. A61F 2/644 623/46 |
| 2002/0162449 A1 | | 11/2002 | Futami et al. |
| 2002/0177905 A1 | * | 11/2002 | Yih .................. A61F 2/644 623/24 |
| 2003/0195637 A1 | * | 10/2003 | Shen .................. A61F 2/60 623/44 |
| 2004/0107008 A1 | * | 6/2004 | Veen .................. A61F 2/644 623/39 |
| 2006/0000510 A1 | | 1/2006 | Henley et al. |
| 2006/0259153 A1 | * | 11/2006 | Harn .................. A61F 2/644 623/44 |
| 2007/0208430 A1 | * | 9/2007 | Gramnas .................. A61F 2/68 623/39 |
| 2008/0058958 A1 | * | 3/2008 | Cheng .................. A61F 2/644 623/39 |
| 2009/0143869 A1 | * | 6/2009 | Cheng .................. A61F 2/644 623/39 |
| 2009/0206648 A1 | | 8/2009 | Jones |

FOREIGN PATENT DOCUMENTS

| | | |
|---|---|---|
| GB | 2037406 A | 7/1980 |
| GB | 2328160 A | 2/1999 |
| WO | 02084423 A1 | 10/2002 |

OTHER PUBLICATIONS

Brochure, "Balance Knee OFM1," OSSUR, 2017, 2 Pages.
Brochure, "Paso Knee," OSSUR, 2017, 3 Pages.
"Paso Knee Instructions for Use," OSSUR, 2017, 76 Pages.
European Office Communication from EP Application No. 13161593.2, dated Aug. 17, 2016.
Extended European Search Report from EP Application No. 13161593.2, dated Jun. 18, 2014.

* cited by examiner

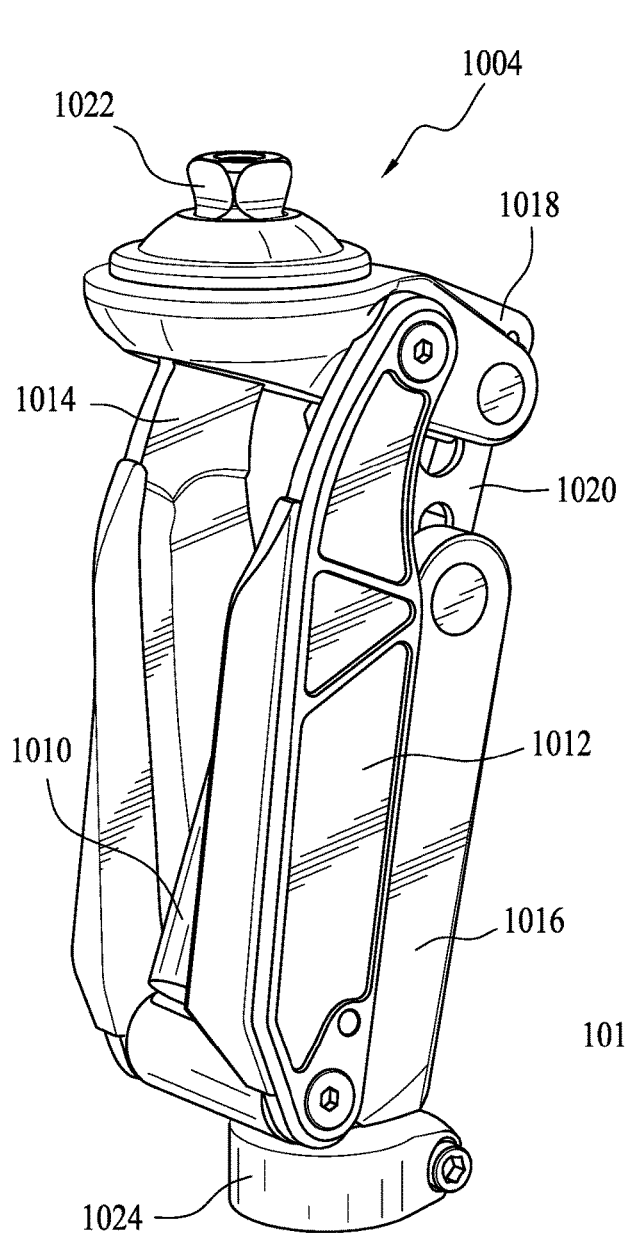
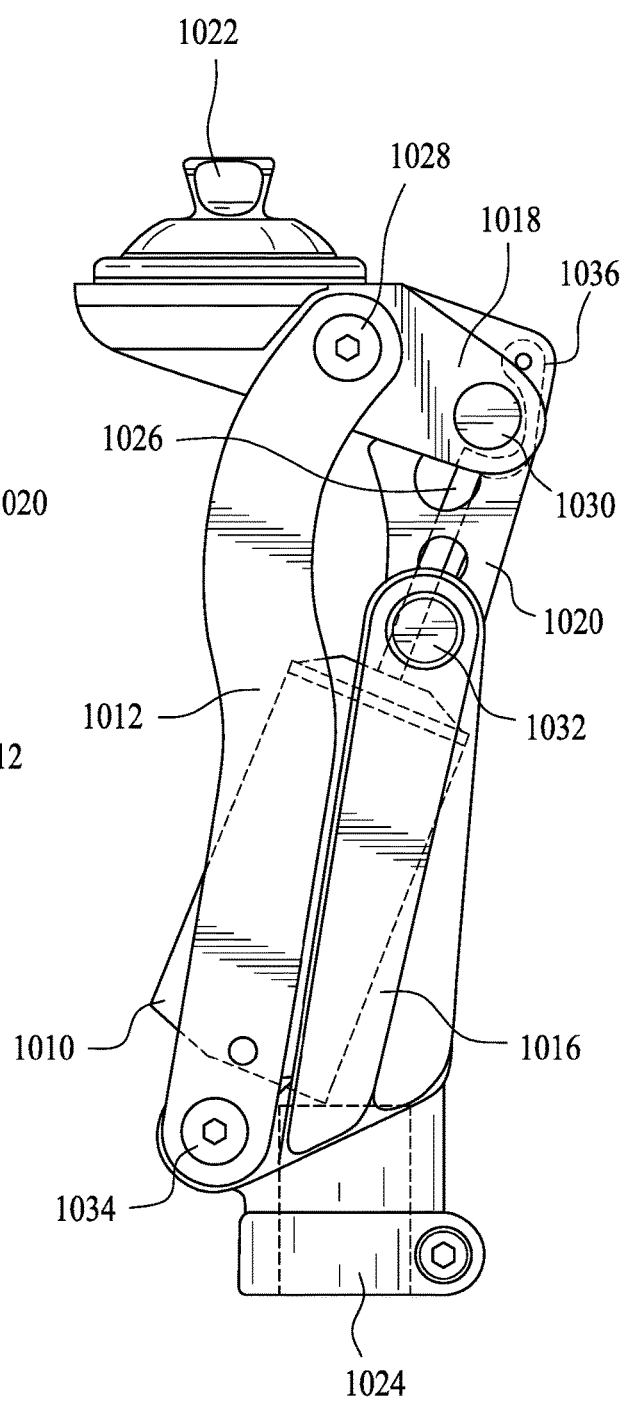
FIG. 2A
FIG. 2B

US 10,918,501 B2

POLYCENTRIC KNEE JOINT HAVING AN ADJUSTMENT-FREE MULTI-STAGE AIR CYLINDER

CROSS-REFERENCE TO RELATED PATENT APPLICATIONS

This application is a continuation-in-part application of U.S. patent application Ser. No. 15/809,222, filed on Nov. 10, 2017, which is a continuation-in-part application of an abandoned U.S. patent application Ser. No. 13/846,026, entitled "ADJUSTMENT-FREE MULTI-STAGE PROSTHESIS AIR CYLINDER AND MULTI-STAGE AIR PRESSURE VALVE THEREOF" and filed on Mar. 18, 2013, which claims priority of Taiwan Application No. 101206148 dated Apr. 5, 2012, by the same inventor of the present application and claims the benefit thereof and incorporates the same by reference.

BACKGROUND OF THE INVENTION

1. Field of the Invention

The present invention relates to a polycentric knee joint including an air cylinder for cushioning, especially to an adjustment-free multi-stage air cylinder that has a multi-stage air pressure valve.

2. Description of the Prior Art(s)

An air cylinder controls air pressure by sliding a piston. Since air is compressible, the air can be compressed by the piston and be accumulated in the air cylinder. As an external forces applied to the piston is removed, the compressed air pushes the piston to slide backwardly.

The air cylinder can be also applied to a prosthesis joint that is used as a medical device which provides cushioning functions and serves as an alternative of a joint. In a first conventional prosthesis joint, a cushioning air cylinder cushions a specific magnitude of compression force. For example, a user that walks slowly can use a cushioning air cylinder for slow walking speed. When the user wants to do a brisk walk or go jogging, the cushioning air cylinder for slow walking speed has to be replaced by another cushioning air cylinder which is adapted to brisk walking speed. In other words, the user has to prepare two or more kinds of cushioning air cylinders, so as to be adapted himself to different walking speeds.

In a second conventional cushioning air cylinder, a cushioning force can be controlled by setting different cushioning modes. Thus, the user can adjust the cushioning air cylinder according to the walking speeds, so as to allow the cushioning air cylinder to form suitable cushioning force. However, although the second conventional cushioning air cylinder can be individually used and be adapted to the different walking speeds, no matter how ways to adjust the cushioning air cylinder are modified, the user still needs to actively adjust the cushioning air cylinder whenever the walking speeds changes. Moreover, when a wrong cushioning mode is set, the cushioning air cylinder may be damaged and the user may feel uncomfortable or be injured due to the lack of the cushioning function.

The prosthetic knee may depend on the activity level or levels of a user. In a prosthetic knee, friction plays a significant role in the extent a knee bends during gait of the user. Mechanical knees employ constant friction and may adjust the level of friction according to the extent a user walks.

A common mechanical knee is a polycentric knee, which has a variable center of rotation and offers stability throughout all phases of gait. A linkage system of the polycentric knee has a collapsing feature which allows the knee to collapse better during the swing phase of gait. The swing phase control can be mechanical friction or hydraulic resistance. Hydraulic and pneumatic knees allow adjustment of walking speed by hydraulics (either liquid or air) within the knee. As a person's walking speed increases or decreases, the hydraulics adjust to control the speed at which the shin of the prosthesis swings forward and bends backwards. Hydraulics can be used with a polycentric knee.

SUMMARY OF THE INVENTION

The main objective of the present invention is to provide an adjustment-free multi-stage prosthesis air cylinder. The prosthesis air cylinder has an air cylinder body, a piston assembly, a first check valve, and a multi-stage air pressure valve. In the context of a prosthesis air cylinder, the air cylinder may be provided in combination with a polycentric knee joint.

The polycentric knee joint may include the prosthetic knee having a housing, parallel anterior links, a posterior link, and a chassis. The anterior links are pivotally connected to both the housing and the chassis, whereas the posterior link likewise connects to the housing and the chassis. The prosthetic knee may include an adapter on the housing and an attachment at the base of the chassis. The prosthesis air cylinder preferably has a piston rod pivotally connected to the housing, and a cylinder body pivotally connected anterior links and/or chassis to create airflow resistance according to a user's speed of gait as the polycentric knee articulates through gate.

The air cylinder body has an air chamber and a lower air way. The air chamber is defined inside the air cylinder body. The lower air way formed in a bottom portion of the air cylinder body and has two ends respectively connected to the air chamber and an outside of the air cylinder body.

The piston assembly is slidably mounted on the air cylinder body and has a piston rod, a piston, and an upper air way. The piston rod is mounted through a top portion of the air cylinder body. The piston is mounted in the air chamber of the air cylinder body, is attached to the inner end of the piston rod, and divides the air chamber into an upper air chamber and a lower air chamber. The upper air way is formed in the piston rod and has two ends respectively connected to the outside of the air cylinder body and the upper air chamber.

The first check valve is disposed in the piston and only allows air inside the upper air chamber to flow into the lower air chamber.

The multi-stage air pressure valve is mounted inside the lower air way and has a first component, a second component, two sealing rings, and a resilient element.

The first component has a top part, a protrusion part axially protruding from the top part, a main channel, and a first bypass channel. The main channel penetrates through the first component from the top part to the protrusion part, forms an air inlet on a top surface of the top part, and forms a first air outlet on a bottom surface of the protrusion part. The first bypass channel penetrates through the protrusion part, communicates with the main channel, and forms a second air outlet on the side surface of the protrusion part.

The second component is mounted around the first component and has a bottom part, an extension part, and an outlet channel. The extension part axially protrudes from the bottom part towards the top part of the first component and surrounds the first component. The outlet channel axially penetrates through the bottom part and has a uniform radial width. A widest radial width of the protrusion part of the first component is smaller than the uniform radial width of the outlet channel of the second component. A second bypass channel is defined between the protrusion part of the first component and the second component.

The sealing rings are respectively mounted around a side surface of the top part of the first component and a side surface of the protrusion part of the first component. The second air outlet is disposed between the two sealing rings.

The resilient element is compressible, is mounted in the second component and around the protrusion part of the first component, and has two opposite ends respectively abutting the top part of the first component and the bottom part of the second component.

The top part of the first component is positioned toward the lower air chamber of the air cylinder body and the bottom part of the second component is positioned toward the outside of the air cylinder body.

The first component is slidable in the second component and the protrusion part of the first component is slidable in the outlet channel of the second component and selectively slides into the outlet channel. When the sealing ring on the protrusion part slides along with the first component to slide into the outlet channel of the second component, the sealing ring on the protrusion part abuts the bottom part of the second component and communication between the second bypass channel and the outlet channel is sealed.

The adjustment-free multi-stage prosthesis air cylinder is suitable for being used in a prosthesis joint, which is especially suitable for being used in a knee prosthesis of a leg. When the user walks slowly (usually with a walking speed less than 2-4 km/h), a gas flow rate of the prosthesis air cylinder is relatively higher, so as to quickly discharge the air inside the prosthesis air cylinder. Thus, a longer cushioning stroke can be formed, so as to allow the user to feel comfortable. When the user walks in a high speed (usually with a walking speed around 4-8 km/h), the gas flow rate of the prosthesis air cylinder is automatically reduced. Thus, movement of the piston assembly of the prosthesis air cylinder can be gradually and softly cushioned, so as to allow the user to still feel comfortable.

The air cylinder is arranged in combination with the polycentric knee joint structure, and operates, as explained in the foregoing, to the user's degree of activity and need for safety, particularly during stance phase. It follows that in a polycentric knee, the air cylinder pivotally connects to a housing and anterior links, in combination with a posterior link and a chassis to provide powerful yet precise movements.

The adjustment-free multi-stage prosthesis air cylinder can be easily installed in the prosthesis joint and the user does not have to frequently adjust the prosthesis air cylinder. Moreover, the adjustment-free multi-stage prosthesis air cylinder of the present invention also has a simple structure, lower cost, and long span life.

BRIEF DESCRIPTION OF THE DRAWINGS

FIG. 2A is a perspective view of the prosthetic knee joint of FIG. 1;

FIG. 2B is a side elevational of the prosthetic knee joint of FIG. 2A;

DETAILED DESCRIPTION OF THE PREFERRED EMBODIMENTS

Environment and Context

FIG. 1A schematically depicts a prosthetic leg and foot assembly 1000 for a residual limb 1010. The assembly 1000 includes a socket assembly 1002 that embraces the residual limb 1010, a prosthetic knee joint 1004 connected to the socket assembly 1002, a pylon 1006 connecting to the prosthetic knee joint 1004, and a foot 1008 connecting to the pylon 1006.

To understand the operation of the prosthetic knee described herein, a basic discussion of the gait cycle is required. A gait cycle defines the movement of the leg between successive heel contacts of the same foot. The gait cycle has two phases: stance and swing. The stance phase has three time periods: heel-strike, mid-stance and toe-off.

During mid-stance, the knee joint will be at full extension. An actual knee joint will have flexion between heel-strike and mid-stance and between mid-stance and toe-off. This is called "stance flexion." Not all prosthetic joints provide for stance flexion, and for those that do, they are mechanically complex, expensive, or both. These prosthetic joints typically require frequent maintenance and replacement. The amount of stance flexion required can vary from user to user, while most prosthetic joints have no adjustability.

Maximum flexion of the knee joint, while walking, will occur at the end of the toe-off phase. Maximum flexion is typically determined in part by the speed at which a person is walking. The faster a person walks the greater maximum flexion, while the slower a person walks, the lesser maximum flexion. In a natural knee, maximum flexion can be controlled and limited via the musculature of the leg. In a prosthetic knee joint, some artificial means of controlling and limiting maximum flexion are typically provided. Immediately following the end of the toe-off phase begins the swing phase.

While the stance phase has three time periods, the swing phase has two time periods: acceleration and deceleration. The acceleration phase begins immediately following the maximum flexion during the toe-off phase. During the acceleration phase, the lower portion of the leg, comprising the shin and foot, swings back towards full extension. In a natural knee joint, a deceleration phase follows the acceleration phase, during which the lower portion of the leg continues to swing towards full extension. Some prosthetic joints do not provide for any deceleration during the swing phase. Other prosthetic joints provide deceleration by using costly and bulky hydraulic or pneumatic cylinders. The deceleration required can vary from user to user, while most prosthetic joints have no adjustability.

EXEMPLARY EMBODIMENT

Figure 1:
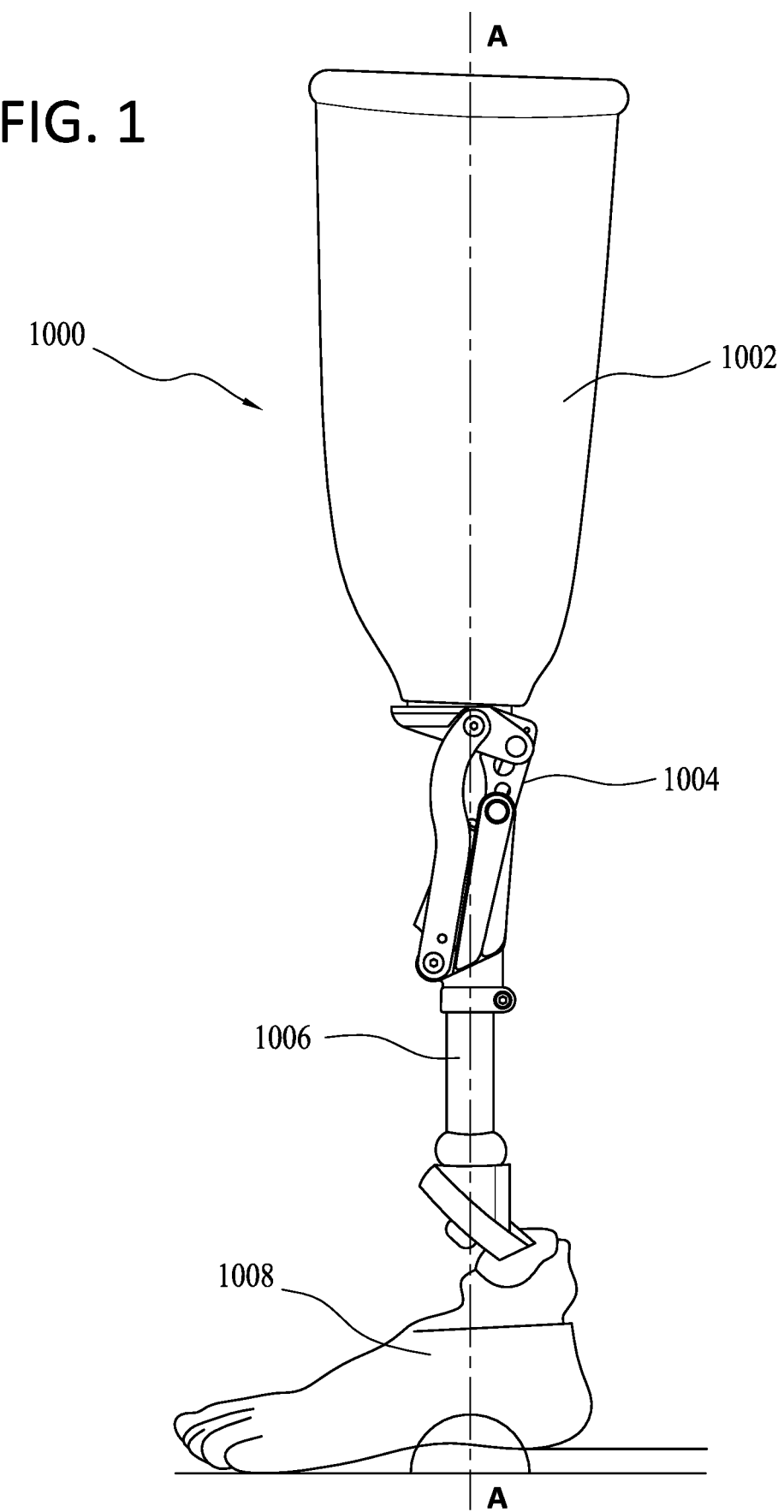
FIG. 1 is a schematic view showing a prosthetic leg and foot assembly, with a prosthetic knee joint having an adjustment-free multi-stage prosthesis air cylinder.
Figure 3:
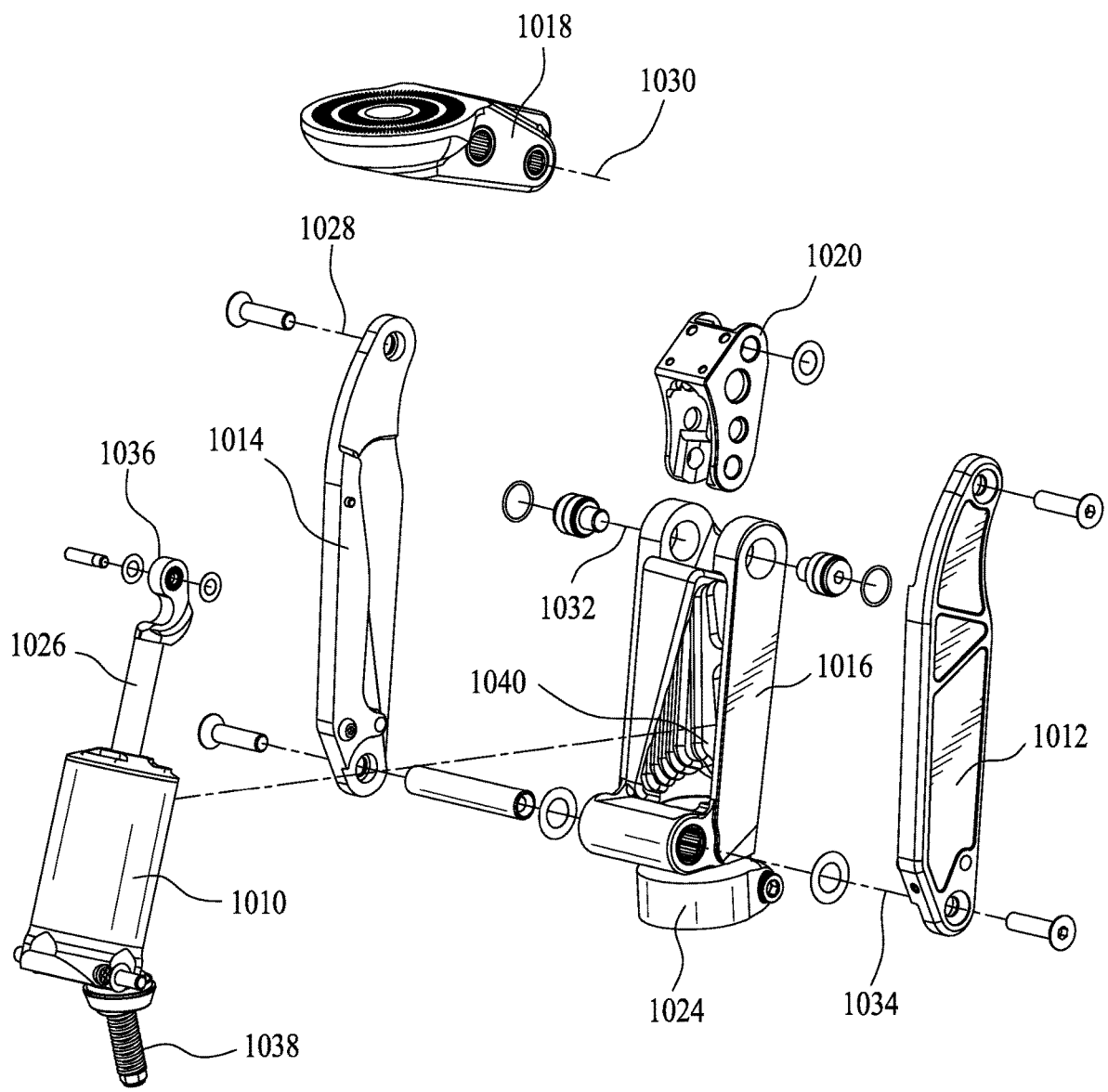
FIG. 3 is an exploded view of the prosthetic knee joint of FIG. 1.

FIGS. 2A, 2B and 3 show an exemplary prosthetic knee joint having an adjustment-free multi-stage prosthesis air cylinder 1010 in the polycentric knee joint 1004 of FIG. 1. Aside from the air cylinder 1010, the polycentric knee joint 1004 may be of conventional construction including a housing 1018, first and second anterior links 1012, 1014, a chassis 1016, and a posterior link 1020. An adapter 1022 is located on the housing 1018, and another adapter 1024 is located on the chassis 1016.

The first and second anterior links 1012, 1014 connect at the anterior side of the housing 1018 at pivot points 1028, and at the anterior side of the chassis 1016 at pivot points 1034. The posterior link 1020 connects to the housing 1018 at pivot point 1030, and to the chassis at pivot point 1032.

The air cylinder 1010 has a piston rod 1026 arranged to extend within the posterior link 1020 and has a proximal link arranged to pivotally connect 1036 to the housing 1018 at a proximal end. The air cylinder 1010 pivotally connects to the first and second anterior links 1012, 1014 at a distal end. The chassis 1016 defines a cavity 1040 in which extends at least part of the air cylinder 1010. The air cylinder 1010 defines a shaft 1038 extends through the adapter 1024.

Figure 6:
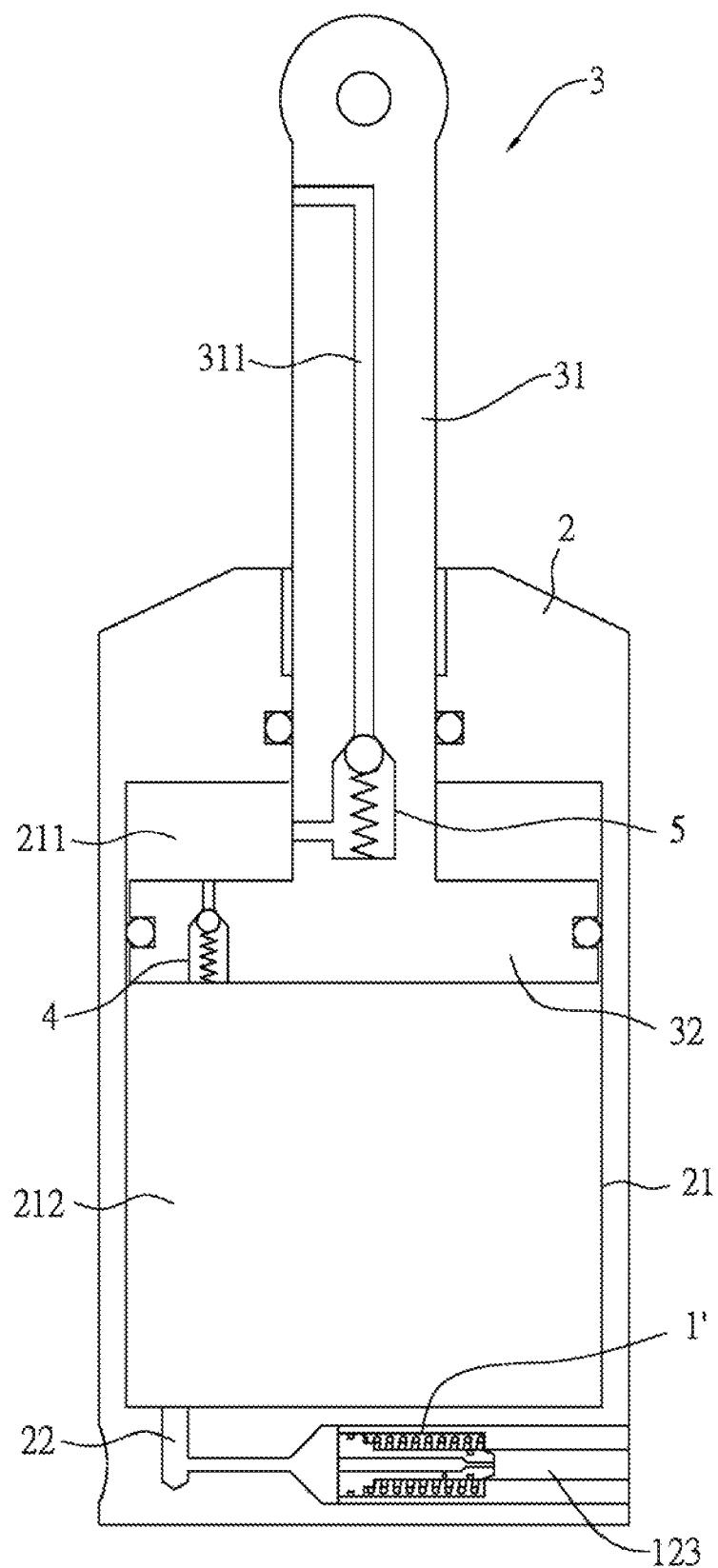
FIG. 6 is a cross-sectional schematic view of a first embodiment of an adjustment-free multi-stage prosthesis air cylinder in accordance with the present invention.
Figure 6A:
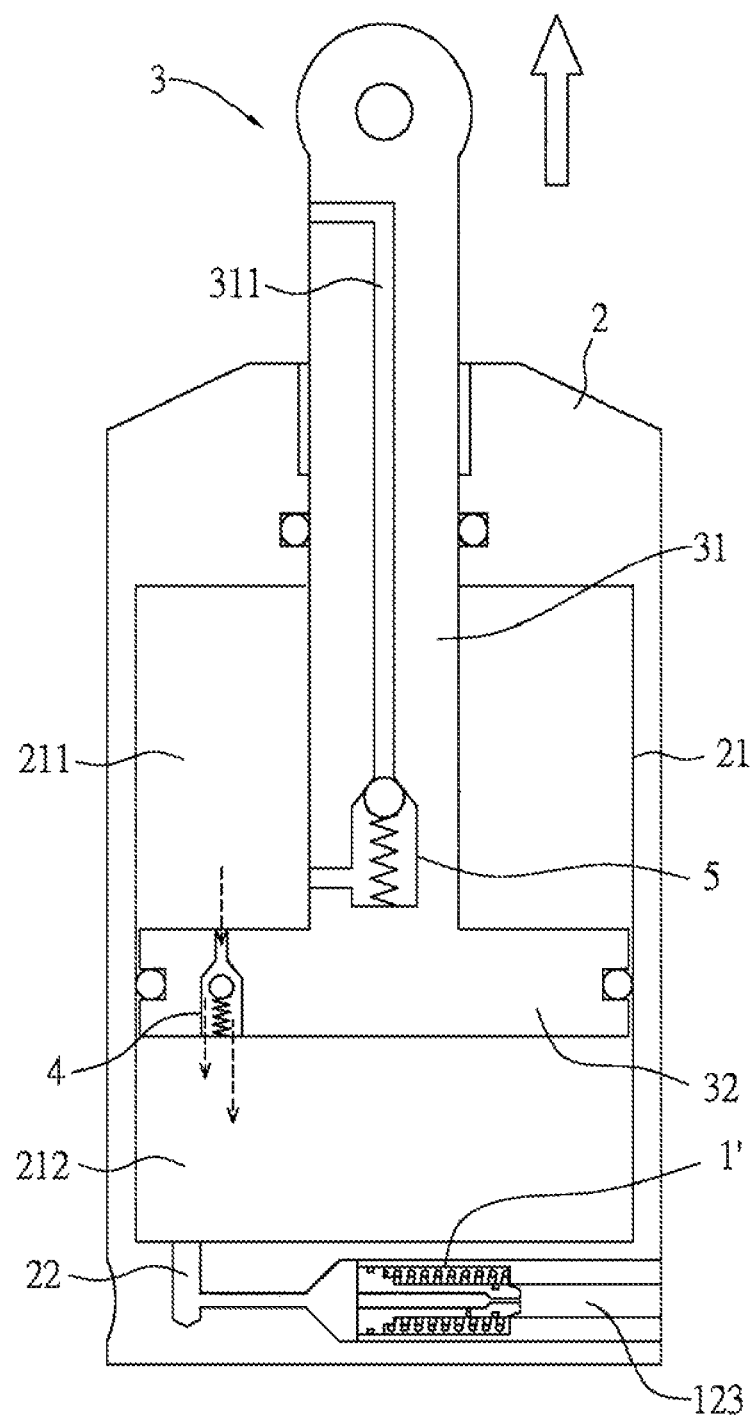
FIG. 6A is a cross-sectional schematic view of the adjustment-free multi-stage prosthesis air cylinder in FIG. 6, showing the piston assembly sliding upwards.
Figure 7:
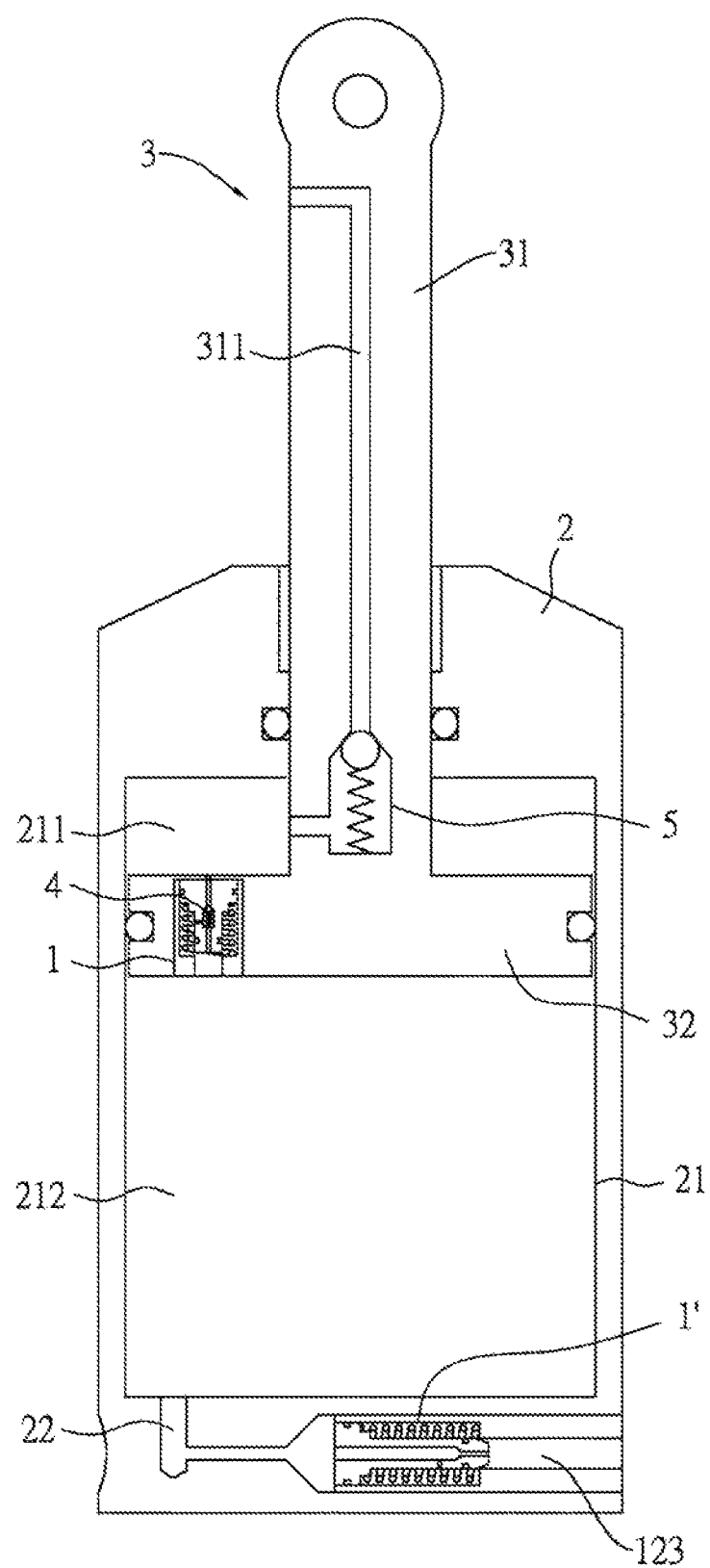
FIG. 7 is a cross-sectional schematic view of a second embodiment of an adjustment-free multi-stage prosthesis air cylinder in accordance with the present invention.

Referring to FIGS. 6 and 7, an adjustment-free multi-stage prosthesis air cylinder in accordance with the present invention comprises at least one multi-stage air pressure valve 1, 1'. Each of the at least one multi-stage air pressure valve 1, 1' is disposed in an air passage of the adjustment-free multi-stage prosthesis air cylinder, so as to form cushioning effects and supporting forces according to different air pressures.

Embodiment 1

Figure 4A:
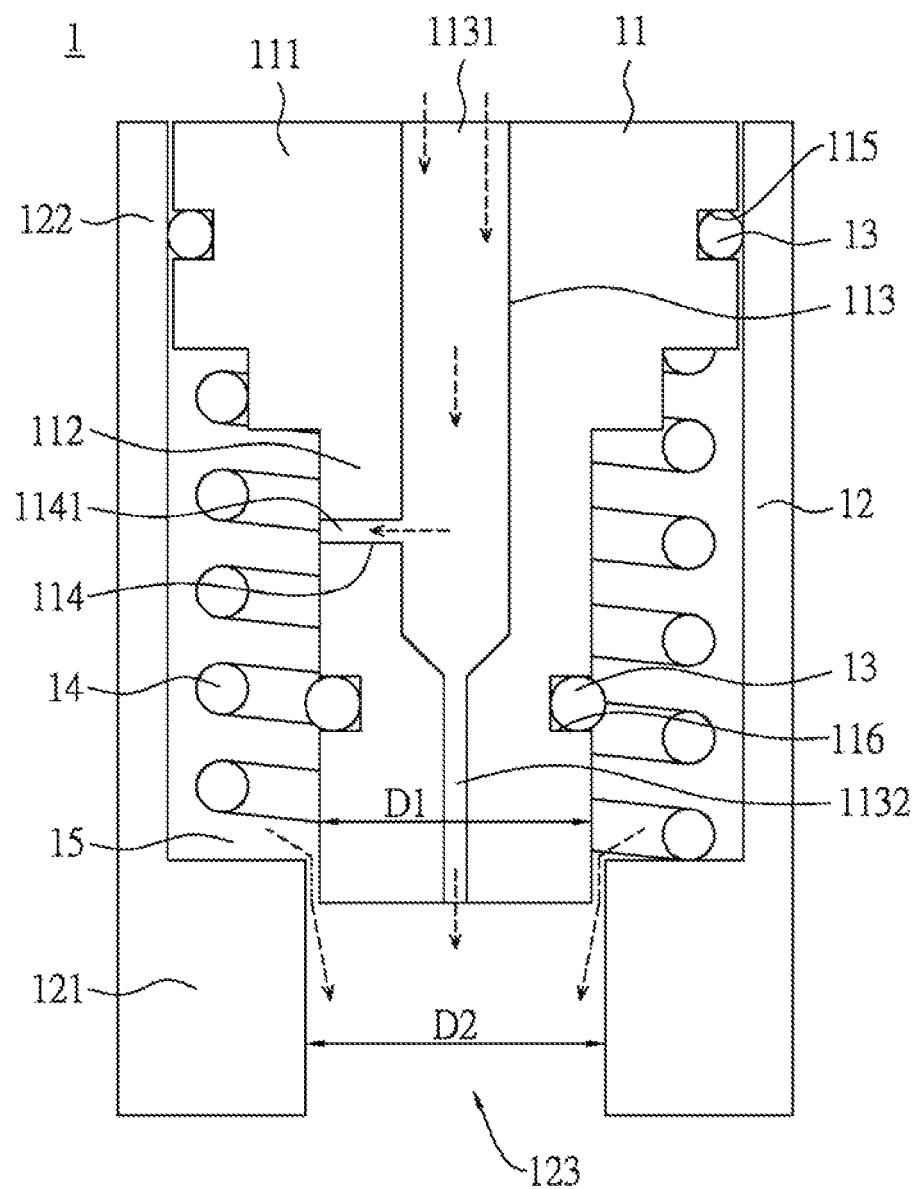
FIG. 4A is a cross-sectional schematic view of a first embodiment of a multi-stage air pressure valve of an adjustment-free multi-stage prosthesis air cylinder in accordance with the present invention, shown uncompressed.

Referring to FIG. 4A, in a preferred embodiment, the multi-stage air pressure valve 1 includes a first component 11, a second component 12, two sealing rings 13, and a resilient element 14.

The first component 11 includes a top part 111, a protrusion part 112, a main channel 113, a first bypass channel 114, a first ring groove 115, and a second ring groove 116.

The top part 111 has a top surface and a side surface. The protrusion part 112 axially protrudes from the top part 111 and has a bottom surface and a side surface. The bottom surface of the protrusion part 112 and the top surface of the top part 111 are oppositely defined on the first component 11.

The main channel 113 is formed inside the first component 11, penetrates through the first component 11 from the top part 111 to the protrusion part 112, forms an air inlet 1131 on the top surface of the top part 111, and forms a first air outlet 1132 on the bottom surface of the protrusion part 112. The first bypass channel 114 penetrates through the protrusion part 112, communicates with the main channel 113, and forms a second air outlet 1141 on the side surface of the protrusion part 112.

The first ring groove 115 is formed in the side surface of the top part 111. The second ring groove 116 is formed in the side surface of the protrusion part 112. The second air outlet 1141 is disposed between the first ring groove 115 and the second ring groove 116.

The second component 12 is mounted around the first component 11 and includes a bottom part 121, an extension part 122, and an outlet channel 123. The extension part 122 axially protrudes from the bottom part 121 towards the top part 111 of the first component 11 and surrounds the first component 11. The outlet channel 123 axially penetrates through the bottom part 121 and has a uniform radial width D2. A widest radial width D1 of the protrusion part 112 of the first component 11 is smaller than the uniform radial width D2 of the outlet channel 123 of the second component 12.

The first component 11 is slidable in the second component 12. The protrusion part 112 of the first component 11 is slidable in the outlet channel 123 of the second component 12 and selectively slides into the outlet channel 123.

A second bypass channel 15 is defined between the protrusion part 112 of the first component 11 and the second component 12.

The sealing rings 13 are disposed on the first component 11. One of the sealing rings 13 is mounted in the first ring groove 115 of the first component 11 and abuts the extension part 122 of the second component 12, so as to seal a first gap between the top part 111 of the first component 11 and the extension part 122 of the second component 12. The other sealing ring 13 is mounted in the second ring groove 116 of the first component 11 and selectively slides into the outlet channel 123 along with the protrusion part 112 of the first component 11. Accordingly, the second air outlet 1141 is disposed between the two sealing rings 13. The seal ring 13 in the second ring groove 116 seals a second gap between the protrusion part 112 of the first component 11 and the bottom part 121 of the second component 12 when the sealing ring 13 in the second ring groove 116 slides into the outlet channel 123 and abuts the bottom part 121 of the second component 12. Moreover, when the sealing ring 13 in the second ring groove 116 slides into the outlet channel 123, the second bypass channel 15 is sealed.

The resilient element 14 is compressible and is mounted in the second component 12 and around the protrusion part 112 of the first component 11 and has two opposite ends. One of the ends of the resilient element 14 abuts the top part 111 of the first component 11. The other end of the resilient element 14 abuts the bottom part 121 of the second component 12. Specifically, the resilient element 14 may be a compression spring.

Referring to FIG. 4A, when the multi-stage air pressure valve 1 is in use, air flows toward the top surface of the top part 111 of the first component 11. When a compression force that the air exerts onto the first component 11 is smaller than a resilient force of the resilient element 14, the first component 11 does not slide relative to the second component 12 and the seal ring 13 in the second ring groove 116 is position out of the outlet channel 123. Accordingly, the second bypass channel 15 is opened and communicates with the outlet channel 123. The air enters the main channel 113 and flows out of the main channel 113 via the first air outlet 1132 to flow to the outlet channel 123 and then flow out of the multi-stage air pressure valve 1 and via the second air outlet 1141 to flow into the second bypass channel 15. Since the second bypass channel 15 communicates with the outlet channel 123, the air that flows into the second bypass channel 15 further flows through the outlet channel 123 to flow out of the multi-stage air pressure valve 1. Since the main channel 113, the first bypass channel 114, and the second bypass channel 15 are all opened, the multi-stage air pressure valve 1 allows the air to flow with a higher gas flow rate.

Figure 4B:
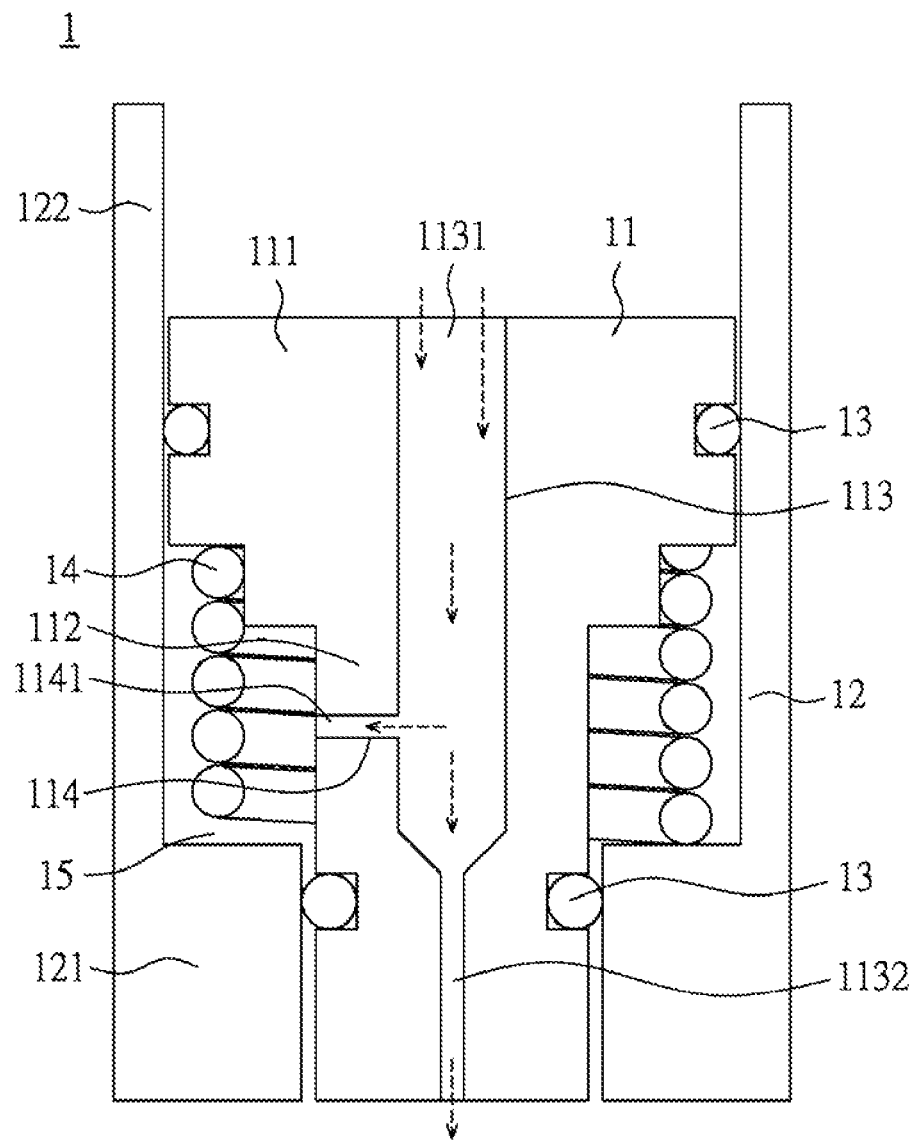
FIG. 4B is a cross-sectional schematic view of the multi-stage air pressure valve in FIG. 4A, shown compressed.

Referring to FIG. 4B, when the compression force that the air exerts on the first component 11 is larger than the resilient force of the resilient element 14, the first component 11 is pushed by the air to slide toward the bottom part 121 of the second component 12 and the protrusion part 112 of the first component 11 slides into the outlet channel 123 of the second component 12. When the sealing ring 13 in the second ring groove 116 also slides into the outlet channel 123, communication between the second bypass channel 15 and the outlet channel 123 is sealed. Thus, the air that flows into the main channel 113 can only flow out of the multi-stage air pressure valve 1 via the first air outlet 1132. Accordingly, the gas flow rate of the air in the multi-stage air pressure valve 1 is lowered.

In addition, the sealing ring 13 in the first ring groove 115 on the top part 111 of the first component 11 prevents the air in the second bypass channel 15 from flowing out of the multi-stage air pressure valve 1 via the first gap between the top part 111 of the first component 11 and the extension part 122 of the second component 12.

Embodiment 2

Figure 5:
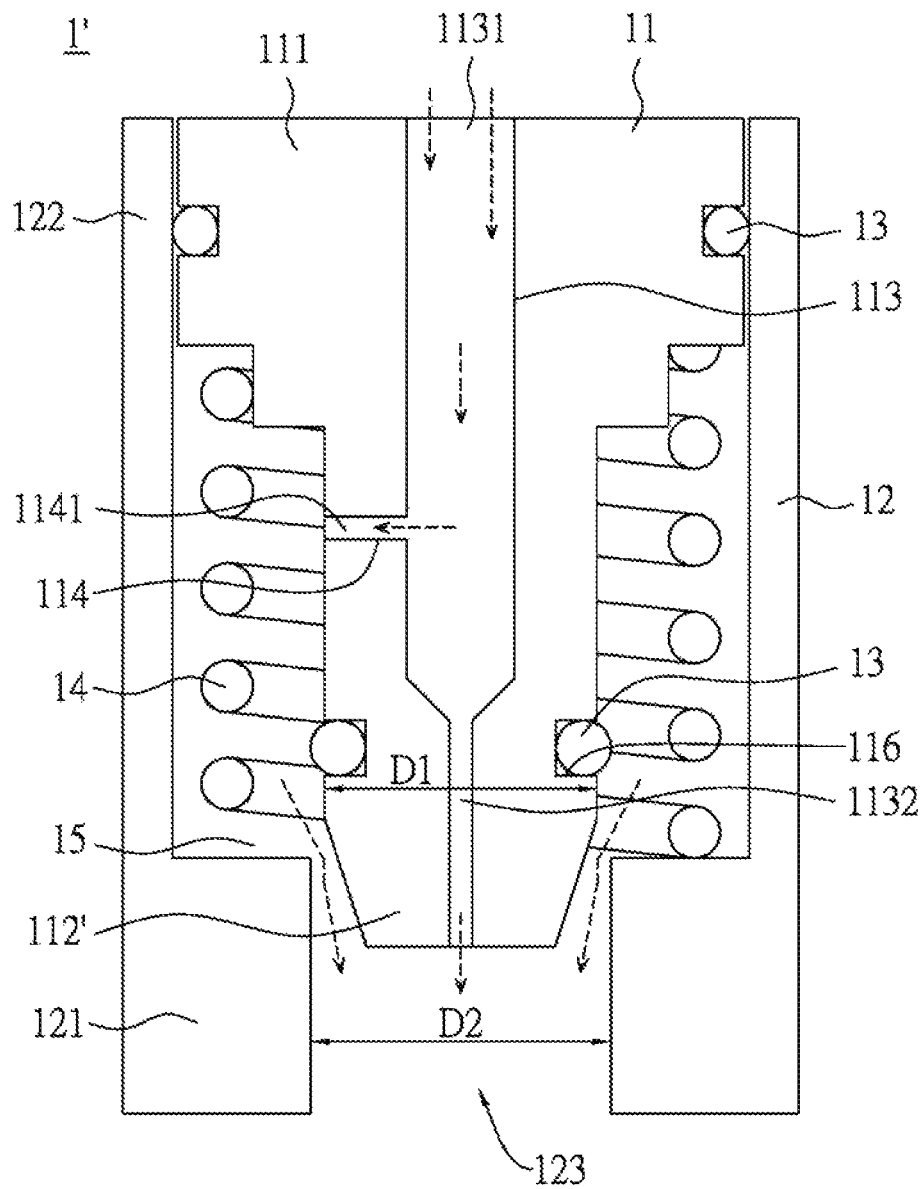
FIG. 5 is a cross-sectional schematic view of a second embodiment of a multi-stage air pressure valve of an adjustment-free multi-stage prosthesis air cylinder in accordance with the present invention, shown uncompressed.

Referring to FIG. 5, in another preferred embodiment of the multi-stage air pressure valve 1', the protrusion part 112' of the first component 11 is tapered from the second ring groove 116 to the bottom surface of the protrusion part 112'. Thus, a width of the second gap between the protrusion part 112' of the first component 11 and the bottom part 121 of the second component 12 varies when the protrusion part 112' slides into the outlet channel 123 of the second component 12. When the sealing ring 13 in the second ring groove 116 slides into the outlet channel 123, the second gap between the protrusion part 112' and the bottom part 121 is sealed.

Referring to FIG. 5, when the multi-stage air pressure valve 1' is in use, air flows toward the top surface of the top part 111 of the first component 11. When the compression force that the air exerts on the first component 11 starts to push the first component 11 to slide toward the bottom part 121 of the second component 12 and the sealing ring 13 in the second ring groove 116 is position out of the outlet channel 123, the main channel 113, the first bypass channel 114, and the second bypass channel 15 are all opened, such that the multi-stage air pressure valve 1' allows the air to flow with a higher gas flow rate.

Figure 5A:
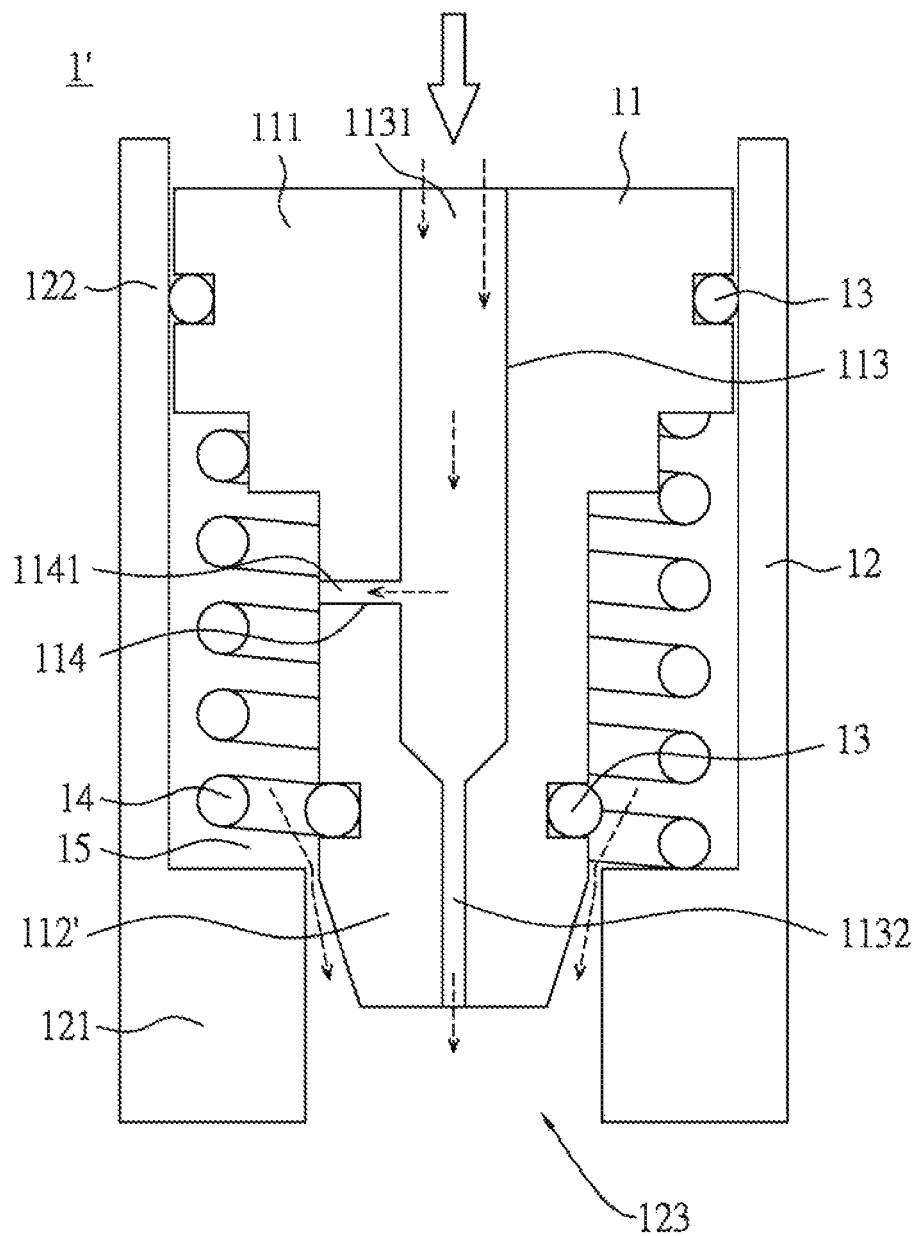
FIG. 5A is a cross-sectional schematic view of the multi-stage air pressure valve in FIG. 5, shown partially compressed.

With further reference to FIG. 5A, since the protrusion part 112' of the first component 11 is tapered from the second ring groove 116 to the bottom surface of the protrusion part 112', the second gap between the protrusion part 112' and the bottom part 121 is gradually narrowed as the protrusion part 112 gradually slides into the outlet channel 123. Accordingly, the gas flow rate of the air in the multi-stage air pressure valve 1' is gradually reduced.

Figure 5B:
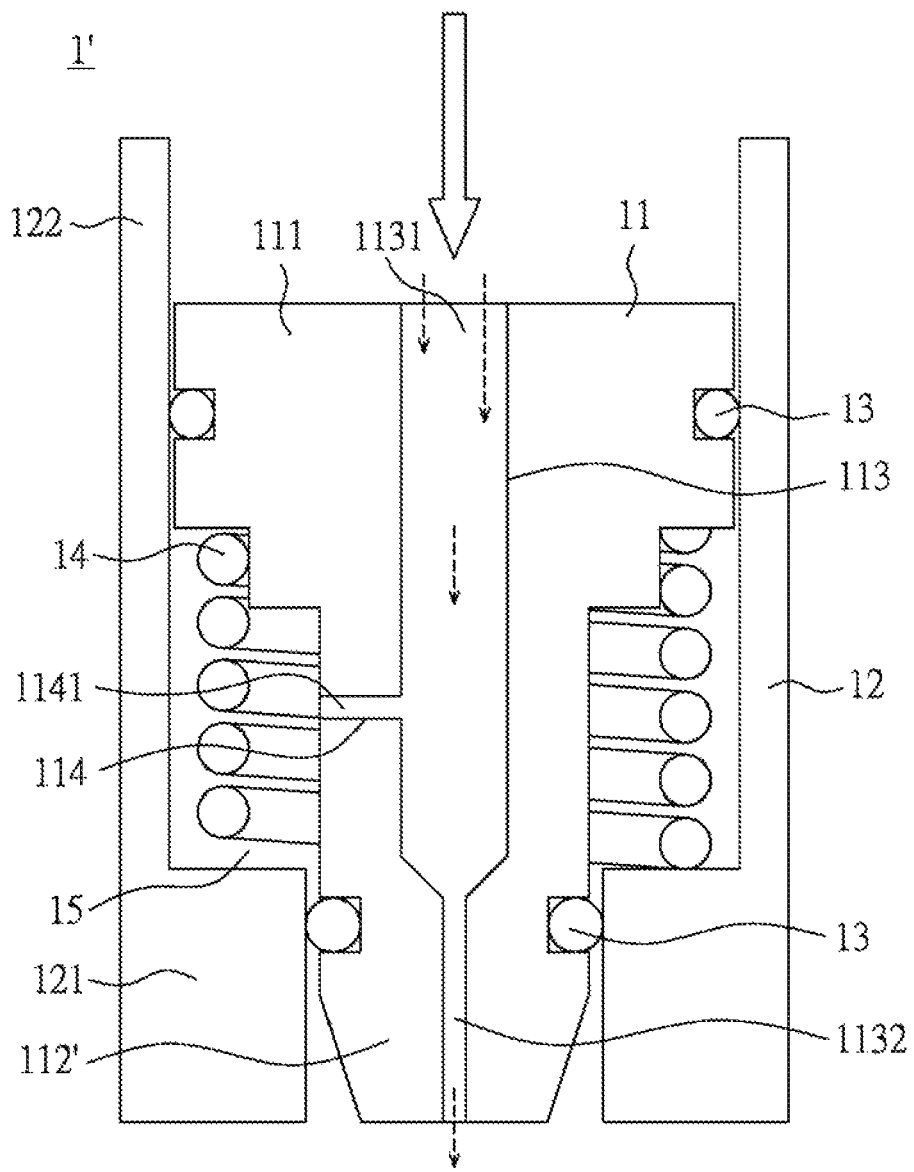
FIG. 5B is a cross-sectional schematic view of the multi-stage air pressure valve in FIG. 5, shown compressed.

With further reference to FIG. 5B, when the sealing ring 13 in the second ring groove 116 slides into the outlet channel 123, the communication between the second bypass channel 15 and the outlet channel 123 is sealed. Accordingly, the gas flow rate of the air in the multi-stage air pressure valve 1' is reduced to a minimum value.

Embodiment 3

Referring to FIG. 6, the adjustment-free multi-stage prosthesis air cylinder with the aforementioned multi-stage air pressure valve 1, 1' can be used in a prosthesis joint. The adjustment-free multi-stage prosthesis air cylinder further comprises an air cylinder body 2, a piston assembly 3, a first check valve 4, and a second check valve 5.

The air cylinder body 2 has a top portion, a bottom portion, an air chamber 21, and a lower air way 22. The air chamber 21 is defined inside the air cylinder body 2. The lower air way 22 is formed in the bottom portion of the air cylinder body 2 and has two ends. The ends of the lower air way 22 are respectively connected to the air chamber 21 and an outside of the air cylinder body 2.

The piston assembly 3 is slidably mounted on the air cylinder body 2 and has a piston rod 31, a piston 32, and an upper air way 311. The piston rod 31 is mounted through the top portion of the air cylinder body 2 and has an inner end and an outer end. The inner end of the piston rod 31 protrudes in the air chamber 21 of the air cylinder body 2. The outer end of the piston rod 31 protrudes to the outside of the air cylinder body 2. The piston 32 is attached to the inner end of the piston rod 31, is mounted in the air chamber 21 of the air cylinder body 2, and divides the air chamber 21 into an upper air chamber 211 and a lower air chamber 212. The upper air way 311 is formed in the piston rod 31 and has two ends. The ends of the upper air way 311 are respectively connected to the outside of the air cylinder body 2 and the upper air chamber 211. As the piston assembly 3 slides back and forth relative to the air cylinder body 2, the piston 32 slides back and forth in the air chamber 21 of the air cylinder body 2 and volumes of the upper air chamber 211 and the lower air chamber 212 are variable.

The first check valve 4 is disposed in the piston 32 and has two ends. One of the ends of the first check valve 4 is connected to the upper air chamber 211. The other end of the first check valve 4 is connected to the lower air chamber 212. The first check valve 4 only allows air inside the upper air chamber 211 to flow into the lower air chamber 212.

The second check valve 5 is disposed in the upper air way 311 of the piston rod 31 and only allows air outside the air cylinder body 2 to flow into the upper air chamber 211.

The multi-stage air pressure valve 1' is mounted inside the lower air way 22. The top part 111 of the first component 11 is positioned toward the lower air chamber 212 of the air cylinder body 2. The bottom part 121 of the second component 12 is positioned toward the outside of the air cylinder body 2.

With further reference to FIG. 7A, when the piston assembly 3 slides upwards, the volume of the upper air chamber 211 is gradually reduced and the volume of the lower air chamber 212 is gradually increased. Accordingly, air pressure in the upper air chamber 211 is gradually increased, the first check valve 4 is opened, and the second check valve 5 is closed, such that the air in the upper air chamber 211 flows to the lower air chamber 212 via the first check valve 4.

Figure 6B:
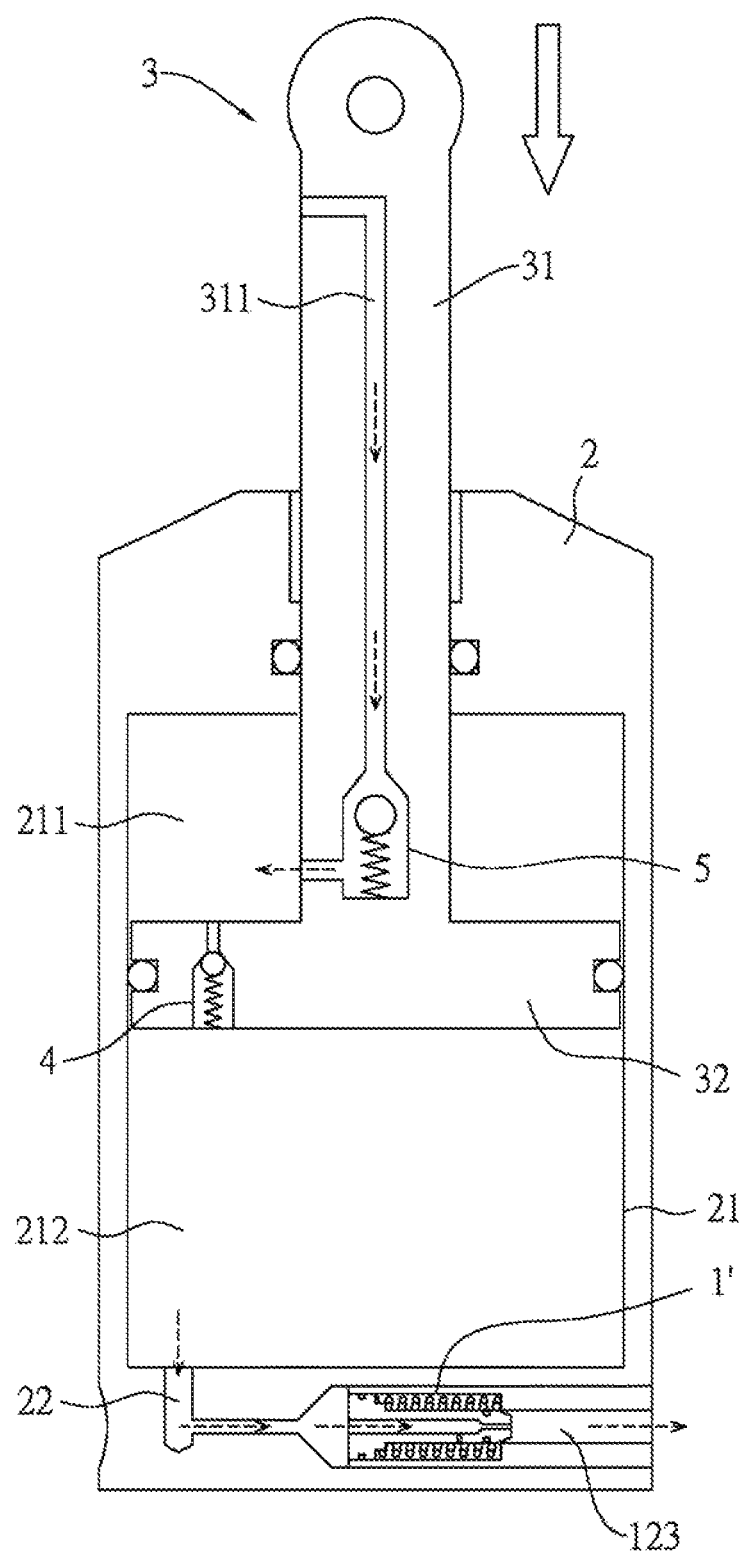
FIG. 6B is a cross-sectional schematic view of the adjustment-free multi-stage prosthesis air cylinder in FIG. 6, showing the piston assembly sliding downwards.

With further reference to FIGS. 6B and 5, when the piston assembly 3 slides downwards, the volume of the upper air chamber 211 is increased and the volume of the lower air chamber 212 is reduced. Accordingly, the air pressure in the upper air chamber 211 is gradually decreased, the second check valve 5 is opened to allow the air outside the air cylinder body 2 to flow into the upper chamber 212, and the first check valve 4 is closed, such that the air in the lower air chamber 212 is compressed by the piston 32 and is forced to flow into the lower air way 22 and flow out of the air cylinder body 2 through the main channel 113, the first bypass channel 114, and the second bypass channel 115 of the multi-stage air pressure valve 1'.

With further reference to FIGS. 7B and 6B, when the piston assembly 3 rapidly downwards, an instantaneous high pressure exerts on the multi-stage air pressure valve 1', such that the first component 11 is pushed toward the bottom part 121 of the second component 12 and compresses the resilient element 14. As the protrusion part 112 of the first component 11 slides into the outlet channel 123 of the bottom part 121 of the second component 12, the communication between the second bypass channel 15 and the outlet channel 123 is sealed. Accordingly, the air that is compressed and is from the lower air chamber 212 can only be discharged from the first air outlet 1132 of the main channel 113.

In conclusion, when the piston assembly 3 slowly slides back and forth, the air in the lower air chamber 212 is discharged through the main channel 113, the first bypass channel 114, and the second bypass channel 115 of the multi-stage air pressure valve 1' (as shown in FIG. 5), so as to form a longer cushioning stroke that allows a user to feel comfortable.

When the piston assembly 3 rapidly slides back and forth, the air in the lower air chamber 212 can only be discharged through the main channel 113 of the multi-stage air pressure valve 1' (as shown in FIG. 5B). Even when the protrusion part 112 of the first component 11 and the second sealing ring 13 around the protrusion part 112 slides into the outlet channel 123 to seal the communication between the second bypass channel 15 and the outlet channel 123, the protrusion part 112 of the first component 11 can still slide forwardly and deeply into the outlet channel 123 of the second component 12, so as to gradually and softly cushion movement of the piston assembly 3 of the prosthesis air cylinder as well as the prosthesis joint.

Embodiment 4

Referring to FIG. 7, in another preferred embodiment of the adjustment-free multi-stage prosthesis air cylinder, two multi-stage air pressure valves 1, 1' are mounted in the adjustment-free multi-stage prosthesis air cylinder. One of the multi-stage air pressure valve 1' is mounted inside the lower air way 22 as described and the other multi-stage air pressure valve 1 is mounted inside the piston 32.

With reference to FIGS. 8 and 5A, in the piston 32, the top part 111 of the first component 11 of the multi-stage air pressure valve 1 is positioned toward the upper air chamber 211 of the air cylinder body 2, the bottom part 121 of the second component 12 of the multi-stage air pressure valve 1 is positioned toward the lower air chamber 212 of the air cylinder body 2, and the first check valve 4 is disposed inside the main channel 113 of the first component 11 and is disposed between the air inlet 1131 and the first bypass channel 114.

The air pressure of the air flowing into the air cylinder body 2 can be preliminarily adjusted through the multi-stage air pressure valve 1 in the piston 32 and then adjusted through the multi-stage air pressure valve 1' in the lower air way 22 of the air cylinder body 2. With the two multi-stage air pressure valves 1, 1' mounted in the piston 2 and in the lower air way 22 of the air cylinder body 2, the air flowing into the prosthesis air cylinder are thoroughly cushioned with multiple stages.

Effects of the Embodiments

The adjustment-free multi-stage prosthesis air cylinder as described is suitable for being used in the prosthesis joint, which is especially suitable for being used in a knee prosthesis of a leg. When the user walks slowly (usually with a walking speed less than 2-4 km/h), the gas flow rate of the prosthesis air cylinder is relatively higher, so as to quickly discharge the air inside the prosthesis air cylinder. Thus, the longer cushioning stroke can be formed, so as to allow the user to feel comfortable. When the user walks in a high speed (usually with a walking speed around 4-8 km/h), the protrusion part 112 of the first component 11 slides into the outlet channel 123 of the second component 12 and the gas flow rate of the prosthesis air cylinder is automatically reduced. Thus, the movement of the piston assembly 3 of the prosthesis air cylinder can be gradually and softly cushioned, so as to allow the user to still feel comfortable.

The adjustment-free multi-stage prosthesis air cylinder as described can be easily installed in the prosthesis joint and the user does not have to frequently adjust the prosthesis air cylinder. Moreover, the adjustment-free multi-stage prosthesis air cylinder of the present invention also has a simple structure, lower cost, and long span life.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

The invention claimed is:
1. A polycentric knee joint having first and second anterior links pivotally connected to a chassis and a housing, and a posterior link pivotally connected to the chassis and the housing, an air cylinder arranged for adjustment-free multi-stage movement and pivotally connecting to the first and second anterior links and the housing, the air cylinder comprising:
 an air cylinder body having
  a top portion;
  a bottom portion, the bottom portion connecting to the first and second anterior links;
  an air chamber defined inside the air cylinder body; and
  a lower air way formed in the bottom portion of the air cylinder body and having two ends respectively connected to the air chamber and an outside of the air cylinder body;
 a piston assembly slidably mounted on the air cylinder body and having
  a piston rod mounted through the top portion of the air cylinder body and having an inner end, the piston rod pivotally connecting to the housing;
  a piston attached to the inner end of the piston rod, mounted in the air chamber of the air cylinder body, and dividing the air chamber into an upper air chamber and a lower air chamber; and an upper air way formed in the piston rod and having two ends respectively connected to the outside of the air cylinder body and the upper air chamber;

a first check valve disposed in the piston and having two ends respectively connected to the upper air chamber and the lower air chamber, and the first check valve only allowing air inside the upper air chamber to flow into the lower air chamber; and a multi-stage air pressure valve mounted inside the lower air way and including
   a first component including
      a top part having a top surface and a side surface;
      a protrusion part axially protruding from the top part and having a bottom surface and a side surface, wherein the bottom surface of the protrusion part and the top surface of the top part are oppositely defined on the first component;
      a main channel formed inside the first component, penetrating through the first component from the top part to the protrusion part, forming an air inlet on the top surface of the top part, and forming a first air outlet on the bottom surface of the protrusion part; and
      a first bypass channel penetrating through the protrusion part, communicating with the main channel, and forming a second air outlet on the side surface of the protrusion part;
   a second component mounted around the first component and including
      a bottom part;
      an extension part axially protruding from the bottom part towards the top part of the first component and surrounding the first component; and
      an outlet channel axially penetrating through the bottom part and having a uniform radial width;
   wherein a widest radial width of the protrusion part of the first component is smaller than the uniform radial width of the outlet channel of the second component; and
   a second bypass channel is defined between the protrusion part of the first component and the second component;
      two sealing rings, one of the sealing rings is mounted around the side surface of the top part of the first component and abutting the extension part of the second component, and the other sealing ring mounted around the side surface of the protrusion part of the first component, wherein the second air outlet is disposed between the two sealing rings; and
      a resilient element being compressible, mounted in the second component and around the protrusion part of the first component, and having two opposite ends respectively abutting the top part of the first component and the bottom part of the second component;
   wherein the top part of the first component is positioned toward the lower air chamber of the air cylinder body; and
   the bottom part of the second component is positioned toward the outside of the air cylinder body;
   wherein the first component is slidable in the second component; the protrusion part of the first component is slidable in the outlet channel of the second component and selectively slides into the outlet channel; and
   when the sealing ring on the protrusion part slides along with the first component to slide into the outlet channel of the second component, the sealing ring on the protrusion part abuts the bottom part of the second component and communication between the second bypass channel and the outlet channel is sealed;

wherein the first and second anterior links each have a proximal end connecting to an anterior side of the housing at a first pivot point and a distal end connecting at the anterior side of a distal end of the chassis at a second pivot point, the posterior link connects to a third pivot point at a posterior side of the housing and connects to the chassis at a fourth pivot point;

wherein the chassis defines a cavity in which extends at least part of the air cylinder and an adapter below the cavity, the air cylinder having a shaft extending through the adapter and the piston rod extends within the posterior link, the piston rod having a proximal link pivotally connected to the housing at a proximal end, the air cylinder pivotally connecting to the first and second anterior links above the first pivot point at the distal end of the first and second anterior links.

2. The polycentric knee joint of claim 1, wherein the first component further includes a first ring groove formed in the side surface of the top part; and a second ring groove formed in the side surface of the protrusion part; and the two sealing rings are respectively mounted in the first ring groove and the second ring groove.

3. The polycentric knee joint of claim 2, wherein the protrusion part of the first component is tapered from the second ring groove to the bottom surface of the protrusion part.

4. The polycentric knee joint of claim 1, further comprising a second check valve disposed in the upper air way of the piston rod and only allowing air outside the air cylinder body to flow into the upper air chamber.

5. The polycentric knee joint of claim 1, wherein the air cylinder is arranged so that when a user walks in a slow speed, a gas flow rate of the air cylinder is relatively higher than when the user walks in a high speed, such that the protrusion part of the first component slides into the outlet channel of the second component to automatically reduce the gas flow rate of the air cylinder.

6. A polycentric knee joint having first and second anterior links pivotally connected to a chassis and a housing, and a posterior link pivotally connected to the chassis and the housing, an air cylinder arranged for adjustment-free multi-stage movement and pivotally connecting to the first and second anterior links and the housing, the air cylinder comprising:
   an air cylinder body having
      a top portion;
      a bottom portion, the bottom portion connecting to the first and second anterior links;
      an air chamber defined inside the air cylinder body; and
      a lower air way formed in the bottom portion of the air cylinder body and having two ends respectively connected to the air chamber and an outside of the air cylinder body;
   a piston assembly slidably mounted on the air cylinder body and having
      a piston rod mounted through the top portion of the air cylinder body and having an inner end, the piston rod pivotally connecting to the housing;
   a first check valve associated with the piston assembly and having two ends respectively connected to an upper air chamber and a lower air chamber of the air chamber, and the first check valve only allowing air inside the upper air chamber to flow into the lower air chamber; and
   a multi-stage air pressure valve mounted inside the lower air way and including
      a first component including a top part having a top surface and a side surface;
a protrusion part axially protruding from the top part and having a bottom surface and a side surface, wherein the bottom surface of the protrusion part and the top surface of the top part are oppositely defined on the first component;
a main channel formed inside the first component, penetrating through the first component from the top part to the protrusion part, forming an air inlet on the top surface of the top part, and forming a first air outlet on the bottom surface of the protrusion part; and
a first bypass channel penetrating through the protrusion part, communicating with the main channel, and forming a second air outlet on the side surface of the protrusion part;
wherein the first and second anterior links each have a proximal end connecting to an anterior side of the housing at a first pivot point and a distal end connecting at the anterior side of a distal end of the chassis at a second pivot point, the posterior link connects to a third pivot point at a posterior side of the housing and connects to the chassis at a fourth pivot point;
wherein the chassis defines a cavity in which extends at least part of the air cylinder and an adapter below the cavity, the air cylinder having a shaft extending through the adapter and the piston rod extends within the posterior link, the piston rod having a proximal link pivotally connected to the housing at a proximal end, the air cylinder pivotally connecting to the first and second anterior links above the first pivot point at the distal end of the first and second anterior links.

7. The polycentric knee joint of claim 6, wherein the air cylinder further comprises a second component mounted around the first component and including
a bottom part;
an extension part axially protruding from the bottom part towards the top part of the first component and surrounding the first component; and
an outlet channel axially penetrating through the bottom part and having a uniform radial width;
wherein a widest radial width of the protrusion part of the first component is smaller than the uniform radial width of the outlet channel of the second component; and
a second bypass channel is defined between the protrusion part of the first component and the second component;
two sealing rings, one of the sealing ring mounted around the side surface of the top part of the first component and abutting the extension part of the second component, and the other sealing ring mounted around the side surface of the protrusion part of the first component, wherein the second air outlet is disposed between the two sealing rings; and
a resilient element being compressible, mounted in the second component and around the protrusion part of the first component, and having two opposite ends respectively abutting the top part of the first component and the bottom part of the second component;
wherein the top part of the first component is positioned toward the lower air chamber of the air cylinder body; and
the bottom part of the second component is positioned toward the outside of the air cylinder body.

8. The polycentric knee joint of claim 7, wherein the first component is slidable in the second component; the protrusion part of the first component is slidable in the outlet channel of the second component and selectively slides into the outlet channel; and
when the sealing ring on the protrusion part slides along with the first component to slide into the outlet channel of the second component, the sealing ring on the protrusion part abuts the bottom part of the second component and communication between the second bypass channel and the outlet channel is sealed.

9. The polycentric knee joint of claim 6, wherein the first component further includes a first ring groove formed in the side surface of the top part; and a second ring groove formed in the side surface of the protrusion part; and the two sealing rings are respectively mounted in the first ring groove and the second ring groove.

10. The polycentric knee joint of claim 9, wherein the protrusion part of the first component is tapered from the second ring groove to the bottom surface of the protrusion part.

11. The polycentric knee joint of claim 6, further comprising a second check valve disposed in an upper air way of the piston rod and only allowing air outside the air cylinder body to flow into the upper air chamber.

12. The polycentric knee joint of claim 1, wherein the air cylinder is arranged so that when a user walks in a slow speed, a gas flow rate of the air cylinder is relatively higher than when the user walks in a high speed, such that the protrusion part of the first component slides into the outlet channel of the second component to automatically reduce the gas flow rate of the air cylinder.

13. In a polycentric knee joint having first and second anterior links pivotally connected to a chassis and a housing, and a posterior link pivotally connected to the chassis and the housing, an air cylinder arranged for adjustment-free multi-stage movement and pivotally connecting to the first and second anterior links and the housing, the air cylinder comprising:
an air cylinder body having
a top portion;
a bottom portion, the bottom portion connecting to the first and second anterior links;
an air chamber defined inside the air cylinder body; and
a lower air way formed in the bottom portion of the air cylinder body and having two ends respectively connected to the air chamber and an outside of the air cylinder body;
a piston assembly slidably mounted on the air cylinder body and having
a piston rod mounted through the top portion of the air cylinder body and having an inner end, the piston rod pivotally connecting to the housing;
a first check valve associated with the piston assembly and having two ends respectively connected to an upper air chamber and a lower air chamber, and the first check valve only allowing air inside the upper air chamber to flow into the lower air chamber; and
a multi-stage air pressure valve mounted inside the lower air way and including
a first component including
a top part having a top surface and a side surface;
a protrusion part axially protruding from the top part and having a bottom surface and a side surface, wherein the bottom surface of the protrusion part and the top surface of the top part are oppositely defined on the first component;
a main channel formed inside the first component, penetrating through the first component from the top part to the protrusion part, forming an air inlet on the top surface of the top part, and forming a first air outlet on the bottom surface of the protrusion part; and
a first bypass channel penetrating through the protrusion part, communicating with the main channel, and forming a second air outlet on the side surface of the protrusion part;
a second component mounted around the first component and including
a bottom part;
an extension part axially protruding from the bottom part towards the top part of the first component and surrounding the first component; and
an outlet channel axially penetrating through the bottom part and having a uniform radial width;
wherein a widest radial width of the protrusion part of the first component is smaller than the uniform radial width of the outlet channel of the second component; and
a second bypass channel is defined between the protrusion part of the first component and the second component;
two sealing rings, one of the sealing rings is mounted around the side surface of the top part of the first component and abutting the extension part of the second component, and the other sealing ring mounted around the side surface of the protrusion part of the first component, wherein the second air outlet is disposed between the two sealing rings; and
a resilient element being compressible, mounted in the second component and around the protrusion part of the first component, and having two opposite ends respectively abutting the top part of the first component and the bottom part of the second component;
wherein the top part of the first component is positioned toward the lower air chamber of the air cylinder body; and
the bottom part of the second component is positioned toward the outside of the air cylinder body;
wherein the first and second anterior links each have a proximal end connecting to an anterior side of the housing at a first pivot point and a distal end connecting at the anterior side of a distal end of the chassis at a second pivot point, the posterior link connects to a third pivot point at a posterior side of the housing and connects to the chassis at a fourth pivot point;
wherein the chassis defines a cavity in which extends at least part of the air cylinder and an adapter below the cavity, the air cylinder having a shaft extending through the adapter and the piston rod extends within the posterior link, the piston rod having a proximal link pivotally connected to the housing at a proximal end, the air cylinder pivotally connecting to the first and second anterior links above the first pivot point at the distal end of the first and second anterior links.

14. The polycentric knee joint of claim 13, wherein the first component is slidable in the second component; the protrusion part of the first component is slidable in the outlet channel of the second component and selectively slides into the outlet channel; and
when the sealing ring on the protrusion part slides along with the first component to slide into the outlet channel of the second component, the sealing ring on the protrusion part abuts the bottom part of the second component and communication between the second bypass channel and the outlet channel is sealed.

15. The polycentric knee joint of claim 13, wherein the protrusion part of the first component is tapered from a second ring groove to the bottom surface of the protrusion part.

16. The polycentric knee joint of claim 13, further comprising a second check valve disposed in an upper air way of the piston rod and only allowing air outside the air cylinder body to flow into the upper air chamber.

17. The polycentric knee joint of claim 13, wherein the air cylinder is arranged so that when a user walks in a slow speed, a gas flow rate of the air cylinder is relatively higher than when the user walks in a high speed, such that the protrusion part of the first component slides into the outlet channel of the second component to automatically reduce the gas flow rate of the air cylinder.

* * * * *